(12) United States Patent
Fox (10) Patent No.: US 7,570,359 B2
(45) Date of Patent: Aug. 4, 2009

(54) ILLUMINATING AND PANORAMICALLY VIEWING A MACROSCOPICALLY-SIZED SPECIMEN ALONG A SINGLE VIEWING AXIS AT A SINGLE TIME

(75) Inventor: John S. Fox, 684 Poinsettia Park South, Encinitas, CA (US) 92024

(73) Assignee: John S. Fox, Encinitas, CA (US)

( * ) Notice: Subject to any disclaimer, the term of this patent is extended or adjusted under 35 U.S.C. 154(b) by 1398 days.

(21) Appl. No.: 10/775,792

(22) Filed: Feb. 9, 2004

(65) Prior Publication Data

US 2008/0055593 A1    Mar. 6, 2008

(51) Int. Cl.
    *G01N 21/25*    (2006.01)
(52) U.S. Cl. .................................................. 356/417
(58) Field of Classification Search .......... 356/416–417
    See application file for complete search history.

(56) References Cited

U.S. PATENT DOCUMENTS 4,309,094 A * 1/1982 Bollen ........................... 396/5
5,126,872 A * 6/1992 Birkle .......................... 356/602
5,452,080 A * 9/1995 Tomiya .................... 356/237.1
7,289,646 B2 * 10/2007 Hirahara et al. ............. 382/110
2003/0072011 A1 * 4/2003 Shirley ........................ 356/601

* cited by examiner

Primary Examiner—Kara E Geisel (57) ABSTRACT

Simultaneous illumination along each of multiple axis for panoramic viewing of a macroscopically-sized specimen along a single viewing axis is realized by dichroic mirrors. Selective control of illumination intensity and/or color(s) of, permissively, each of multiple illuminating lights along multiple illumination axis of the specimen as are induced to fluoresce at corresponding different colors and intensities will all appear clearly visible, and well balanced, in a composite image nonetheless to intrinsically being of greatly differing brightness. Color and intensity calibration of the well-balanced composite image in all its colors and regions may optionally be realized by one or more fluorescent image calibration step wedges. A rule, or grid, scale may be imposed upon the image. The resulting panoramic composite image contains a great deal of quantitative information, being optionally calibrated in any of dimension, scale, overall brightness, the separate intensities of, permissively, each of several separate differently-colored fluorescent emissions.

23 Claims, 3 Drawing Sheets

ILLUMINATING AND PANORAMICALLY VIEWING A MACROSCOPICALLY-SIZED SPECIMEN ALONG A SINGLE VIEWING AXIS AT A SINGLE TIME

REFERENCE TO RELATED PATENT APPLICATIONS

The present patent application is related to U.S. patent application Ser. No. 10/810,993 (now U.S. Pat. No. 7,173,256) for a FLUORESCENT IMAGE CALIBRATION STEP WEDGE, AND USE THEREOF IN ILLUMINATION FOR FLUORESCENT IMAGING AND AUTOMATIC EXPOSURE. The present patent application is related to U.S. patent application Ser. No. 10/788,724 (now U.S. Pat. No. 7,280,726) for CONTROLLED-INTENSITY MULTIPLE-FREQUENCY MULTIPLE-AXIS ILLUMINATION OF MACROSCOPIC SPECIMENS FROM A SINGLE LIGHT SOURCE USING SPECIAL BIFURCATED CABLES.

BACKGROUND OF THE INVENTION

1. Field of the Invention

The present invention generally concerns (1) an apparatus, as are commonly but not exclusively used in laboratories, for illuminating and for viewing a macroscopically-sized specimen, for example a mouse, along a viewing axis, and (2) the methods of using such an apparatus.

The present invention particularly concerns viewing, along a single viewing axis at a single time, a macroscopically-sized specimen panoramically, and over more than one hundred and eighty degrees of viewing angle about the specimen. The specimen may be viewed panoramically in and by its reflection of the illuminating light(s) and/or, more commonly, also in such fluorescent emissions as are induced in the specimen by the illuminating light(s). "Macroscopically-sized" means only that the specimen is not microscopic, and may be observed by the naked eye.

The present invention also particularly concerns image illumination for presenting along a single viewing axis at a single time multiple views, each view along an associated axis, of a specimen. Axial illumination along each axis may be separately independently adjusted so that the resulting image view is selectively balanced in either of intensity and/or color (i.e., wavelength, or frequency). The image views may in particular show fluorescence induced in the specimen (along each, and all, illumination axis) at more than one color (i.e., wavelength, or frequency). These fluorescent image regions of differing colors can be controlled so as to appear in a composite image with roughly equal intensity.

Moreover, and further particularly, the selective illumination along each of multiple axis in accordance with the present invention will be seen to support calibration of the observed intensity of fluorescence at each different color (i.e., wavelength, or frequency), as may occur along each and all viewing axis Still further, and finally, the present invention will be seen to concern a "racetrack", or "cattle chute", direction of live specimens, for example mice into a viewing area where each may be automatically simultaneously (1) illuminated along multiple axis, and panoramically observed along multiple viewing axis, while (2) illumination along each axis such as induces multi-colored fluorescence in the specimen will be balanced so that image regions of different fluorescent coloration are themselves balanced, while (3) the true intensity, and color (wavelength, or frequency) of all images, and image views, and image portions may be quantitatively known.

2. Description of the Prior Art

2.1 General Laboratory Apparatus and Methods for Illumination and Observation of Macroscopically Sized Specimens Apparatus to illuminate and to hold macroscopically-sized specimens for viewing, including viewing as may involve the taking of photographs, are known in the art. These apparatus hold secure a macroscopically-sized specimen to be viewed, including for example a live specimen and more particularly a laboratory animal and still more particularly a mouse, upon a specimen stage. One or more sources of illuminating radiation, most commonly light radiation, are brought to bear upon the held specimen.

The illuminating radiation sources may consist of the emitting end of a fiber optic, a fiber optic bundle, or a light pipe or the like. The illuminating radiation itself may, by way of example, be sufficient so as to induce fluorescence in the specimen, including in a specimen as may have been previously fused with fluorescing agents that most commonly serve to make regions of the specimen that are of interest more visible or otherwise detectable.

The illuminated specimen may be, and commonly is, digitally imaged, but may also and/or alternatively be photographed, including in its emitted fluorescent light.

There images so formed are basically nothing but crude snapshots, normally adjusted only in overall intensity and this only by intervention of the image taker, or researcher, such as by adjustment of the intensity of illumination(s), or the exposure of the camera. These images leave a great deal to be desired. Quite commonly a specimen may be infused with multiple fluorescing agents, or dyes, and/or so that different regions of the specimen fluoresce at different colors, or so that the same region of the specimen, such as growing tumor, will exhibit fluorescence of different colors in differing (but often overlapping) areas resultantly to having been infused with a different fluorescing agent (i.e., dyed) at different times (during the growth of the tumor). Some fluorescent colors in some image regions may be bright and/or extensive, obscuring less bright and/or less extensive regions of other colors nonetheless that all image regions—both bright and dim—are of equal observational significance.

Furthermore, there is commonly no way to calibrate the brightness of the induced fluorescence(s).

Finally, the images are not produced automatically even though an image camera may have any of auto-focus and/or auto-exposure. This is because the composite, multi-color fluorescent image presented to the camera is really an image that must have its intensity (brightness), and/or its color, adjusted in parts, and not (normally) as a whole—which is all that an automatic camera is capable of doing. According that the composite images have not been automatically produced, applicant knows of no attempt in the prior art to automatically position a succession of specimens for automatic imaging, such as, in particular, photographing a succession of live mice.

As background to the present invention, the general nature of imaging, and of photographing, macroscopically-sized specimens is contained in paper #3658-12, *Panoramic epifluorescent visualization of cardiac action potential activity*, pp. 99-107 by Mark A. Bray, Vanderbilt Univ., Nashville, Tenn., USA; Marc Lin, Vanderbilt Univ., Nashville, Tenn., USA; John P. Wikswo, Jr., Vanderbilt Univ., Nashville, Tenn., USA This paper is available, circa 2004, at the Vanderbilt University web sites of one or more of its authors.

2.2 The Utility of Introducing Quantitative Rigor into Observations of Macroscopically Sized Specimens The present and related inventions will generally be seen to be directed to a common goal of imparting the imaging, and photographing, of macroscopic specimens (especially specimens as are caused to fluoresce)—a process generally presently conducted "ad hoc"—with a great deal of scientific rigor.

As of present, circa 2004, the images, or photographs produced by conventional illumination and observation of macroscopically-sized specimens, such as the biological specimen of a mouse, tend to be rather crude. Most typically the mouse will be illuminated so that an region of interest, such as a tumor, previously absorbing fluorescent dye will be caused to fluoresce, and the fluorescent region of the resulting image is indicated only that the mouse has the tumor.

In this rudimentary observation many, many things are lacking.

First, it is not possible to view the mouse specimen along multiple axis, or panoramically around a broad angular field, at the same time. This precludes looking at the same tumor in the mouse from two or more different directions, and from looking at multiple tumors as may exist within different regions of the mouse all at the same time.

Accordingly, it would firstly be useful if a single macroscopically-sized specimen, for example a mouse, could be observed along each of multiple axis, for example left side and right side and fore and aft, all at the same time.

Second, no dimensional scale, either linear or grid, typically accompanies the viewed image of the specimen (the mouse). Such a scale is useful for, by way of example, judging the dimension(s) and volume of the observed tumor. Accordingly, it would secondly be useful if the image of a specimen (for example, a mouse) inherently contained a scale of either the linear or the grid type.

Third, and although it is common for a single specimen to contain multiple fluorescing agents which fluoresce at different colors so as to identify corresponding regions of interest within the (single) specimen, it is not commonly thought to attempt adjustment of the intensity of each color within a resulting composite image. In other words, a body impregnated with fluorescent green dye may appear to fluoresce green light quite brightly while another body (or the same body or portion thereof as may have picked up red fluorescent dye at a different time and/or to a different extent) may, under the same common illumination, fluoresce red light quite dimly. Nonetheless that the body, or tumor, fluorescing green shows brightly in the image, and the body, or tumor, fluorescing red shows but dimly in the image, the "green" tumor or stage may be of equal size and/or interest to the "green" tumor. What looks bright, and what looks dim, in the composite image is, of course, a function of the efficiency of the uptake of the fluorescent dyes, the efficiency of the illumination excitation of each, and the efficiency of each dye to fluoresce, among other factors.

Although not common, it is, of course, possible to use multiple illumination sources of different intensities and/or frequencies, independently adjusting selecting illumination frequencies and adjusting the intensity of each so that the resulting "green" tumor and "green" tumor images in the composite are somewhat comparable. The related invention for CONTROLLED-INTENSITY MULTIPLE-WAVELENGTH MULTIPLE-AXIS ILLUMINATION OF MACROSCOPIC SPECIMENS FROM A SINGLE LIGHT SOURCE FROM SPECIAL MASKS, FILTERS AND/OR BIFURCATED CABLES will be seen to deal in an elegant way with this challenge of exciting fluorescent emissions of different colors so that the differently colored areas of a composite image appear comparable. The viewing apparatus of the present invention will be seen to be fully compatible with the related invention, which uses bifurcated cables. However, the viewing apparatus of the present invention will also be seen to be fully suitable for use with multiple light sources that are independently controlled in color and/or, most commonly, intensity.

Accordingly, it would thirdly be useful if each of multiple regions fluorescing at different colors within a single composite image of a specimen (for example, a mouse) could be independently adjusted in intensity, clearly rendering visible in the composite image those things and/or regions that the researcher and image taker desires to be well seen, while suppressing within the composite image other things and/or regions that are deemed unimportant. It would be especially useful if this selective differential "highlighting" of each of multiple colors of fluorescent emission could somehow be realized from but a single, common, illuminating light source.

Some little thought will reveal, however, that should such control be given to the image maker, then it may become impossible to know what has been done in manipulation of the composite image and its several colors, and to know what imaged things and/or regions "really" look like under "normal", or known predetermined, conditions. It is thus problematic that no scale of the intensity(ies) and/or colors (i.e., wavelengths, or frequencies) of (potentially several different) fluorescent emission(s) typically accompanies the viewed image of the specimen (the mouse). Such an intensity and/or color would be scale is useful for, by way of example, judging how bright or how dim, or of exactly what color(s), were things and/or regions appearing in the composite image—nonetheless that the appearance of things or regions within this composite image may have been enhanced, or attenuated in intensity, or may even be "off-shade" in color (i.e., wavelength, or frequency)—under normal, standard, and predetermined illumination conditions.

Accordingly, it would fourthly be useful if the image of a specimen (for example, a mouse) inherently contained a scale of by which any of the intensity(ies), color(s), or, as even more exotic criteria seldom useful, radiation temperature might be accurately known. The color scale might be broken down into hue, chroma (purity, or saturation) and brightness (value). In this manner a viewer of a composite image might be able to say: "I see by comparison to a scale that is within the selfsame image that this clearly visible first object (or area) fluoresced green, and that it was in fact quite bright, even to the point of obscuration, until intentionally diminished in intensity. Meanwhile I also see by comparison to another portion of the same scale, or another scale also contained within the image, that this equally clearly visible second object (or area) fluoresced green, but only dimly so, and that this second object has intentionally been accentuated in intensity by action of the image maker. In fact, by comparison to the scale, I can quantitatively determine the absolute quantitative brightness (i.e., intensity) of each and all of the green and the red fluorescing regions. Still further, I can see by comparison to this same scale that both the colors green are red are in hue (i.e., wavelength, or frequency) precisely as would be expected as emissions from their respective fluorescent dyes. I must thus assume that there is no extraneous colored light falling upon the specimen, and that I am looking at a true and accurate image of fluorescent emissions from the specimen, without anything else or any extraneous color contamination of this image."

Fifth, it would be useful if, in addition to making better and more comprehensive images bearing improved quantitative information, if it were possible to produce such images with a greater degree of automation. It would in particular be useful if in the imaging of large numbers of live animals, such as mice, the successive images of successive mice—no matter how widely differing in their fluorescing tumors or the like— could not only be automatically correctly quantitatively recorded, image after image, but if the mice could be "herded" past an imaging point, with each mouse in turn being automatically imaged.

SUMMARY OF THE INVENTION

The present and related inventions generally contemplate imparting scientific rigor to the imaging, and photographing, of macroscopic specimens, especially such specimens as are caused to fluoresce. In so doing a more complete, even a panoramic, composite image will be developed.

The physical scale and dimensions of items within this composite, potentially panoramic, image may be known and compared by reference to only the image itself, and require no external metric.

The specimen within this composite panoramic image will not only be appropriately illuminated in all spatial locations and orientations, and will so appear uniformly "well-illuminated" within the composite image, but all such fluorescent emissions at variously colors and intensities as are induced in the specimen, and as appear in the composite image, can be separately and independently adjusted in intensity within the composite image. The adjustment of the intensity of the various differently colored fluorescent regions within the composite image permits this composite image to appear harmonious without having one color "flood out" another, and so as to permit maximum effect extraction of information from the composite image. In simplest terms, bright features of one color are not permitted to obscure dim features of another color within the composite image.

Nonetheless that color intensities within the composite image are adjustable, the true colors, including each of (1) hue, (2) chroma (purity, or saturation) and (3) brightness (value) of potentially each of several differently-colored bodies (or regions) within the composite image may be rigorously quantitatively known and compared by reference to only the image itself, and require no external metric.

Nonetheless that the composite image is (1) panoramic, (2) balanced in the intensity of its several differently colored regions, and (3) contains quantitative scale and/or color and/or intensity information, this composite image may be automatically generated. Moreover, a succession of such composite images of different specimens, for example mice, may normally be obtained automatically simply by forcing, or by gating, the mice past a stationary imaging point, or "station".

The particular present invention that is the subject of this specification disclosure thus contemplates elevating and improving a common specimen illumination apparatus from the present level of a mere laboratory equipment of simple purpose to a precision, and an automated, tool. By use of this precision automated tool images of macroscopically-sized specimens are improved. The composite images are improved in (1) angular field of view, including by multi-axis viewing and even by panoramic viewing.

The composite images are further improved in that (2) the intensity of one or more fluorescent fields (even as may be of different colors/frequencies) appearing within the composite, multi-axis and multi-field, image are selectively controlled along each illumination axis by varying the intensity and/or wavelength (frequency) of excitation illumination along that axis. The intensity is so controlled so as to make the image "well balanced", and revelatory of maximum information. Moreover, in accordance with a related invention employing bifurcated fiber optic cables—the use of which related invention is not mandatory with the present invention—this intensity-controlled excitation illumination may be efficiently, and effectively, realized along each of multiple illumination, and viewing, axis.

Considering such "well-revealed" image information, the composite images are still further improved in that (3a) scale, and/or (3b) image color (i.e. wavelength, or frequency), and/or (3c) image intensity, in all the various (normally fluorescent) fields of the composite image may be each be known, and quantitatively known.

Finally, these information-rich precision composite images are (4) easily and automatically obtained, including from one imaged specimen to next as a succession of live specimens are passed seriatim in front of an imaging point, or "station".

1. Realization of the Improved Composite Images of the Present Invention 1.1 Multi-Axial, and Panoramic, Viewing and Images The improvement to the (1) angular field of view is realized by both illuminating a specimen along multiple axis all at the same time, and by conducting light (which may be reflected, and/or, more commonly, emissive, light) from the specimen along optical paths (which multiple optical paths, or viewing axis, overlap a portion of each of the multiple illumination axis) until the multiple optical paths become joined into a single, primary, viewing axis whereat a panoramic composite specimen image may be viewed all at one and the same time. This composite panoramic specimen image is essentially realized by use of dichroic mirrors. The preferred apparatus of the present invention commonly permits that more than one-hundred and eighty angular degrees (180°), and most commonly about two hundred and seventy angular degrees (270°), and even an entire, three hundred and sixty angular degree (360°) "surround", image view is possible. Such a panoramic view precludes the necessity of imaging, and photographing, multiple sides of a single specimen, and permits the entire specimen to be imaged for viewing and/or photographing at one single time with one camera (and one camera calibration) only.

Note that the illumination axis proceeding through each dichroic mirror overlaps in part the optical path of any fluorescent light induced in the specimen which fluorescent light, when emitted from the specimen, is reflected towards the primary viewing axis by the same dichroic mirror. In simple terms, illuminating light proceeding inward to impinge upon the specimen overlaps, and proceeds in partially in the same optical path, as will emitted fluorescent light proceeding outward from the specimen. In the transmissions and reflections that occur in these partially overlapping illumination and viewing optical paths, it will be understood by a practitioner of the optical arts that a dichroic mirror is sensitive to color (wavelength, or frequency) in its selective (1) transmission or (2) reflection. In accordance with the present invention, the illuminating light is normally of a relatively shorter (and more energetic, $E=h\nu$) wavelength (i.e., of a relatively higher frequency), as is well capable of exciting fluorescence. This light is substantially passed through the dichroic mirror. Meanwhile, the induced fluorescent light is necessarily of a lower energy, and a relatively longer wavelength (i.e., a relatively lower frequency), and is substantially reflected by the dichroic mirror. Accordingly, the optical paths of the present invention operate with good efficiency with, in particular, little light being lost (through non-reflection from the dichroic mirror) from the fluorescent emissions of the specimen. This conservation of light can be important.

1.2 Improved Automatic Selective Illumination Color (Intensity) and/or Color (i.e., Wavelength, or Frequency) Control Along Each of Multiple Specimen Illumination Axis so as to Produce Composite Images that are Balanced in Multiple Colors and Regions of Fluorescence The improvement providing (2) selective illumination color (intensity) and/or wavelength (frequency) control along each of, permissively, multiple specimen illumination axis not only permits that (a) different physical portions of a three-dimensional macroscopic specimen, such as a mouse, may be selectively differently illuminated in intensity as best viewing dictates, but also that (b) the intensity(ies) of differing color (i.e., wavelength (frequency)) regions of a composite image as appear along any, and all, viewing axis may be selectively controlled. The (a) selective adjustment of overall illumination intensity along each combined illumination and viewing axis permits that, regardless or physical orientation of the specimen and ambient laboratory lighting, there are no dark, nor under-illuminated, regions of the specimen as seen along any viewing axis. The (b) selective adjustment of the intensities and/or colors (i.e., wavelengths, or frequencies) of each of multiple illuminating lights is perhaps more profound in that this permits that differently colored fluorescent emissions induced in the same, or in different, regions of the specimen may all be simultaneously viewed at roughly the same intensity to the eye, or to the camera.

It should be understood that heretofore a macroscopic specimen, such as a mouse, that is treated with multiple fluorescent dyes so as to show, by fluorescent emissions of differing colors, associated multiple phenomena has normally shown brightly in some fluorescent colors and/or regions, and dimly in others. This occurred because the specimen was commonly subjected to the same overall illumination, most normally from above (in support of observation along but one single viewing axis), and often with one or more lights that were of but a single color (i.e., wavelength, or frequency) if not also intensity. The apparatus and method of the present invention permit an investigator to "draw out" all portions of a multi-colored, multi-field, image to a desired intensity and contrast in real time, and in common.

This image formation process of the present invention is superior to attempting to induce image contrast of selected colors, or fields, within the image by digital manipulation of the composite image because in so doing (1) dim portions of the image may never have been adequately exposed so as to permit full image data recovery while, most importantly, (2) there is little or no traceability, nor calibration, to the digital image manipulation. Indeed, it nearly amounts to fraud to manipulate an image advanced for scientific purposes in a manner where no one can actually determine what the investigator actually saw.

In accordance with the present invention, the (2) selective illumination color (intensity) and/or wavelength (frequency) control along each of, permissively and preferably, multiple specimen illumination axis may is realized by an electronic control path. An optical sensor senses each pertinent color (as is normally due to fluorescence), most preferably along each observation path, and produces a signal that, in a rudimentary embodiment, is used to adjust the intensity, or the color, or both the intensity and the color of that illumination source, located along that illumination path which is associated with the observation path, that is inducing the associated fluorescent emission. Thus, in the rudimentary embodiment, a illumination light source is automatically electronically adjusted in intensity and/or color so as to induce such fluorescent emission in the specimen as will, in the composite image, show at the desired intensity.

Different illumination axis associated with different observation, or viewing, axis can simultaneously be differently illuminated. For example, a single tumor fluorescing at a single color within a single mouse might be near to the right side of the mouse so as to show relatively brightly (in the composite image) along a right side viewing axis while showing but relatively dimly along a left side viewing axis. Of course, the dim left-side tumor image may be as, or more, important of observation than the bright right-side tumor image. In accordance with automated control of the present invention, the left side of the specimen mouse would normally be more brightly illuminated, enhancing fluorescent emission, than would the right side of the same mouse.

The (2) selective illumination color (intensity) and/or wavelength (frequency) control along each of, permissively and preferably, multiple specimen illumination axis of the present invention is fully compatible with, and is preferably used in conjunction with, a related invention contained within the related patent application for CONTROLLED-INTENSITY MULTIPLE-WAVELENGTH MULTIPLE-AXIS ILLUMINATION OF MACROSCOPIC SPECIMENS FROM A SINGLE LIGHT SOURCE FROM SPECIAL MASKS, FILTERS AND/OR BIFURCATED CABLES The most preferred apparatus for multi-color (dual color) illumination—even as may occur along some four illumination axis (specimen left, right, front and rear)—employs two only lamps each of which can have its light output adjusted. The light output is commonly so adjusted by changing the (d.c.) voltage to the lamp, thus proportionately (within the range of use) changing the light output of the lamp. The lamp light output or each lamp is then preferably projected through a color, or neutral density, filter into a fiber optic bundle at one of the two ends of a bifurcated (or "X" cross) fiber optic cable. The light outputs of both lamps—which are most commonly at different intensities and also different colors (i.e., wavelengths) especially after filtering—are joined in the bifurcated a fiber optic cable so that they are randomized, with each light being sent to the single end of the bifurcated cable (or the opposite two ends of the "X"-cross cable). Thus fifty percent of the light at each operative end of the cable, which light serves to illuminate the sample, is resulting from one of the independently controlled light sources, and fifty percent is resulting from the other independently controlled light source. Still other things are facilitated by the preferred bifurcated cables. The illuminating light(s) from multiple sources can be blended, and selectively attenuated and/or color filtered, in each of multiple illumination paths. Generally, however, for purposes of the present invention it need only be understood that the related invention teaches an improved, but not a necessary, apparatus and method for the generation of the precision, controlled, illumination lighting that the present invention teaches how to use.

1.3 Quantitative Rigor in the (Composite, Balanced) Images Obtained

The (3) capacity to calibrate the intensity of one or more fluorescent fields (even as may be of different colors, meaning wavelengths or frequencies) within the composite, multi-axis and multi-field, image provides, in a manner substantially heretofore unrealized, complete rigor in the self-calibration of images obtained for scientific purposes. Consider the idea of the previous paragraph that dimly fluorescing fields of one color within the a composite multi-color may, by selectively enhancement of such illumination as induces fluorescence at that color, be enhanced in brightness. Does this not amount to the same image manipulation, and possible scientific fraud? It does not because, in accordance with the present invention, the intensities of each and all colors of the image are calibrated, normally by a scale that shows within the image itself. An investigator may thus observe, by way of example, the spread of a tumor (or tumors) in a macroscopic biological specimen such as a mouse as the mouse is imaged in plural fluorescent colors at and upon each of plural associated events.

For example, the extent of a tumor (or tumor phenomena) type "A", such as may be, by way of example, showing fluorescent green in a composite image may be clearly observed nonetheless that the actual green fluorescent light emissions would be, but for boosting the associated illumination, quite weak. Meanwhile, and continuing with the example, the extent of a tumor (or tumor phenomena) type "B", such as may, by way of example, show bright fluorescent red in the composite image may also be clearly observed in the same composite image, meaning only that both tumors are simultaneously well and properly exposed. The viewer need only to look at color intensity scales in both (1) green and (2) red appearing directly within the image (normally in an image area at the border of a photograph, and outside the imaged specimen proper) to realize that the red fluorescent light emission was actually of much greater intensity than was the green fluorescent light emission.

(Persons not laboratory biologists may be confused: why not simply show—to such extent possible in a single image— that the green-fluorescing tumor (or tumor phenomena) is brighter than the green-fluorescing tumor (or tumor phenomena)? Reasons include that (1) the photochromic efficiency of the green and the red fluorophores, or dyes, may not be equal, (2) the green and the red fluorophores, or dyes, may not have bound with equal efficiency to their respective tumors (or to disparate phenomena of a single tumor) "A" and "B", and (3) nonetheless that the green image is intrinsically less bright, it may be of consummate importance.)

This "color and intensity calibration" is realized by a "fluorescent image calibration step wedge", which device is the subject of the related patent application for FLUORESCENT IMAGE CALIBRATION STEP WEDGE, AND USE THEREOF IN ILLUMINATION FOR FLUORESCENT IMAGING AND AUTOMATIC EXPOSURE. For purposes of the present invention it need only be realized that (1) this calibration device, and/or also any of (2) filters, and/or (2) scale and/or grid masks, may all be readily used to good advantage in the multiple illumination, and imaging, optical paths of the apparatus of the present invention.

1.4 Automated Production of (Composite, Balanced, Quantitative) Specimen Images

Finally in accordance with the present invention—the (4) automated image production being firstly realized by automated selective specimen illumination (as in (3) above) so that, the specimen being optimally illuminated in all colors (i.e., wavelengths, or frequencies) along all axis so as to produce composite images well balanced in all color (i.e., wavelength, or frequency) fields—a photograph may simply be automatically focused and automatically exposed.

This automatic image exposure in accordance with the present invention suffices to work, of course, only because the specimen is properly illuminated, meaning illuminated (along each illumination axis) so as to produce an image wherein all fluorescing regions will show relatively uniformly, and well. Moreover, the (4) automated image production is further, and secondly, realized by (1) confining the live specimens, such as mice, to "racetrack", or a "cattle shoot", configuration where the mice must in any movement pass an imaging point, or station, single file, and then (2) detecting when a mouse is at the imaging point, or station, with photoelectric sensor, proximity sensor, heat sensor or the like so as to trigger (at some milliseconds after illumination has been automatically properly adjusted) the exposure of the camera.

Nonetheless that this automatic illumination and imaging in accordance with the present invention may readily be envisioned, it is remarkable. Fat mice and thin mice, light mice and dark mice, dirty mice and clean mice, sick mice and well mice, and all mice as may in general look quite different particularly including in their fluorescent emissions, will all photograph well, mouse after mouse. Moreover, when the photographs are later referenced, as during a clinical drug trial, it is possible, by reference to scales embedded within each, to make a quite definitive, and quantitative, statement as to what exactly each photograph shows.

2. An Apparatus for Illuminating a Macroscopically-Sized Specimen for Observation Along a Single Viewing Axis Therefor, in one of its aspects the present invention is embodied in an apparatus for illuminating a macroscopically-sized specimen for, upon at least one time, observation along a single viewing axis.

The apparatus includes (1) a stage for supporting a specimen to be observed; (2) one or more first illumination sources radiatively illuminating the specimen upon the stage so that at least some radiation directly reflected from the specimen will be returned along the viewing axis; (3) at least one dichroic mirror positioned so that at least a portion of the specimen not directly observable along the viewing axis will be reflected in the mirror so as to become observable along the viewing axis; and (4) one or more second illumination sources radiatively illuminating the specimen on the stage through the at least one dichroic mirror so that at least some radiation reflected from that region of the specimen not directly observable along the viewing axis will become reflected by the dichroic mirror and will become observable along the viewing axis.

The at least one dichroic mirror commonly consists of number of dichroic mirrors at least two of which mirrors are oppositely positioned about the specimen upon the stage upon the stage. In this manner (1) radiation directly reflected from the specimen, and/or (2) fluorescent emission induced in the specimen, directly along the viewing axis permit of an observation called a "top" view while (3) radiation directly reflected from the specimen, and/or (4) fluorescent emission induced in the specimen, passing through the at least two dichroic mirrors permits of observations called "left" and "right" side views.

Commonly at least one of the one or more first illumination sources is directly illuminating the specimen upon the stage. Still more commonly, two or more first illumination sources directly illuminate the specimen upon the stage, at least one through a dichroic mirror.

Preferably at least one of the first and the second illumination sources is a fiber optic illumination source.

The radiation emitted from at least one of the first and the second illumination sources is commonly suitable so as to induce fluorescent emission in the specimen. Often multiple fluorescent emissions at more than one color are induced, and are variably induced dependent upon both the (1) color(s) (i.e., wavelength(s), or frequency(ies)) of the one or more illuminating lights.

At a location between the at least one dichroic mirror and the specimen upon the stage the preferred apparatus optionally further includes an element affecting both the illuminating, and also the reflective and/or emissive, light(s). This element is of the general class of a "filter", as such word is broadly interpreted.

The element may in particular be (5a) a selectively regionally transparent and opaque grid or rule mask. This mask selectively blocks both radiation from the at least one second illumination source through the at least one dichroic mirror to the specimen, and also such radiation reflected from the specimen as is further reflected by the at least one dichroic mirror along the viewing axis, so that a grid pattern or rule scale visually appears upon an image of those specimen regions that are illuminated through, and that are viewed through, the mask.

The apparatus can alternatively, or additionally, hold at the same location(s) elements in the form of (5b) one or more color filters.

Finally, the apparatus can alternatively, or additionally, hold at the same location(s) elements in the form of (5c) one or more fluorescent image calibration step wedges, as are taught in the related patent application.

The apparatus may have, and preferably does have, a first electronic feedback loop by which the intensity of the illuminating lights, preferably along each separate illumination axis, is controlled, and most preferably independently controlled, in accordance, illuminating light by illuminating light, in intensity and/or color (i.e., wavelength, or frequency) in accordance that another color field, normally resulting from fluorescence induced within the specimen, is either bright or dim (along the corresponding axis).

The apparatus further preferably has another, second, electronic control whereby a sensor, preferably an optical sensor, of the presence of a specimen within a viewing area, or "station", triggers the exposure of a photograph.

3. Improvements to an Apparatus Holding and Illuminating a Macroscopically-Sized Three-Dimensional Specimen In another of its aspects the present invention may be considered to be embodied in improvements to an apparatus for illuminating a macroscopically-sized specimen, these improvements being directed to enabling panoramic viewing of more than one-half of the angular field of the specimen at one time.

This improvement includes (1) a dichroic mirror positioned so that at least a portion of the specimen that is not directly observable along the viewing axis will be reflected in the mirror so as to become observable along the viewing axis; and (2) an illumination source illuminating the specimen on the stage through the at least one dichroic mirror. By this structure at least some illumination arising from the illumination source that is reflected from that region of the specimen not directly observable along the viewing axis will become reflected by the dichroic mirror and will become observable along the viewing axis. Thus more than one-half of the angular field of the specimen is panoramically viewable along the single viewing axis at the one time.

Preferably the two dichroic mirrors are oppositely positioned about axis. An illumination source or sources then serve to illuminate the specimen through each of the two dichroic mirrors. Any (1) illumination directly reflected from the specimen along the viewing axis, plus any (2) fluorescent emissions induced in the specimen directly along the viewing axis, permit an observation called a "top" view. Meanwhile radiation from the specimen that is reflected by each of the two dichroic mirrors simultaneously permits observations called left and right side views.

Further preferably, the illumination source serves to illuminate the specimen through the dichroic mirror with radiation suitable to induce fluorescent emission in the specimen.

Optionally a selectively regionally transparent and opaque grid or rule mask may be located between the dichroic mirror and the specimen upon the stage. This mask serves to selectively blocking both illumination from the illumination source passing through the dichroic mirror to the specimen, and also illumination reflected from the specimen as is further reflected by the dichroic mirror along the viewing axis, so that a grid pattern or rule scale visually appears upon an image of those regions of the specimen's surface that are illuminated through, and that are viewed through, the mask.

Optionally a color filter may be located between the dichroic mirror and the specimen upon the stage.

Optionally a fluorescent image calibration step wedge may be located between the dichroic mirror and the specimen upon the stage.

4. A Method of Illuminating a Macroscopically-Sized Specimen for Observation Along a Single Viewing Axis In yet another of its aspects the present invention may be considered to be embodied in a method of illuminating a macroscopically-sized specimen for, upon at least one time, observation along a single viewing axis.

The method includes (1) supporting a specimen to be observed upon a stage; (2) first radiatively illuminating the specimen upon the stage so that at least some radiation directly reflected from the specimen will be returned along the viewing axis; (3) positioning a dichroic mirror so that at least a portion of the specimen not directly observable along the viewing axis will be reflected in the mirror so as to become observable along the viewing axis; and (4) second radiatively illuminating the specimen on the stage through the dichroic mirror so that at least some radiation reflected from that region of the specimen not directly observable along the viewing axis will become reflected by the dichroic mirror and will become observable along the viewing axis.

The (3) positioning is most preferably of at least two dichroic mirror mirrors oppositely about the specimen upon the stage. In this manner radiation directly reflected from the specimen along the viewing axis permits an observation called a top view while radiation from the specimen reflected by each of the two dichroic mirrors permits observations called left and right side views.

The (2) first radiatively illuminating preferably serves to directly illuminate the specimen upon the stage. Moreover, this (2) first radiatively illuminating is still more preferably with visible light from a fiber optic illumination source.

Either the (1) first radiatively illuminating, or the (2) second radiatively illuminating, or both the first and the second radiative illuminating is preferably with radiation suitable so as to induce fluorescent emission in the specimen.

Still further in the method may transpire the interposing of a selectively regionally transparent and opaque grid or rule mask between the dichroic mirror and the specimen upon the stage. This mask serves so as to selectively block radiation from the second radiatively illuminating en route from the dichroic mirror to the specimen, and also some of this same radiation that, as reflected from the specimen, is en route from the specimen to the dichroic mirror. It makes that a grid pattern or rule scale will visually appear upon an image of those specimen regions that are illuminated through, and that are viewed through, the mask.

Still further in the method may transpire the interposing of a color filter between the dichroic mirror and the specimen upon the stage.

Still further in the method may transpire the interposing of a fluorescent image calibration step wedge between the dichroic mirror and the specimen upon the stage.

The intensity of the illuminating lights is preferably controlled in a first electronic feedback loop proceeding from an optical sensor, preferably filtered so as to sensitive to a fluorescent emission desired to be detected. A separate control path preferably separately controls intensity along each separate illumination axis.

A camera is preferably triggered for exposure of a photograph in accordance that a specimen is detected to be within a predetermined viewing area, or "station".

These and other aspects and attributes of the present invention will become increasingly clear upon reference to the following drawings and accompanying specification.

BRIEF DESCRIPTION OF THE DRAWINGS

Referring particularly to the drawings for the purpose of illustration only and not to limit the scope of the invention in any way, these illustrations follow:

FIG. 3, consisting of FIGS. 3a and 3b, are respective detail side and diagrammatic perspective views of a portion of either the rudimentary, or the preferred, illumination and viewing apparatus in accordance with the present invention previously respectively seen in FIGS. 1a and 1b.

DESCRIPTION OF THE PREFERRED EMBODIMENT

The following description is of the best mode presently contemplated for the carrying out of the invention. This description is made for the purpose of illustrating the general principles of the invention, and is not to be taken in a limiting sense. The scope of the invention is best determined by reference to the appended claims.

Although specific embodiments of the invention will now be described with reference to the drawings, it should be understood that such embodiments are by way of example only and are merely illustrative of but a small number of the many possible specific embodiments to which the principles of the invention may be applied. Various changes and modifications obvious to one skilled in the art to which the invention pertains are deemed to be within the spirit, scope and contemplation of the invention as further defined in the appended claims.

Figure 1A:
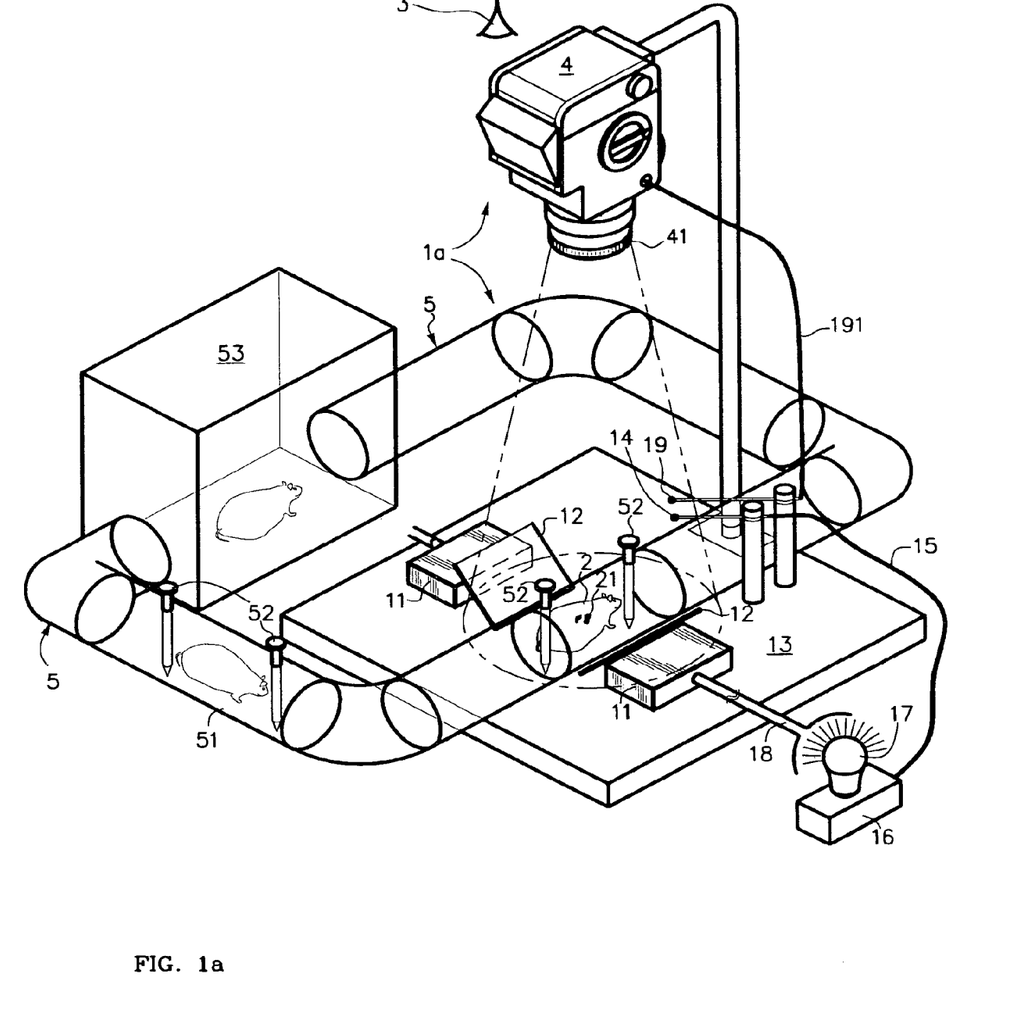
FIG. 1a is a diagrammatic view of a basic, rudimentary, illumination and viewing apparatus in accordance with the present invention.
Figure 1B:
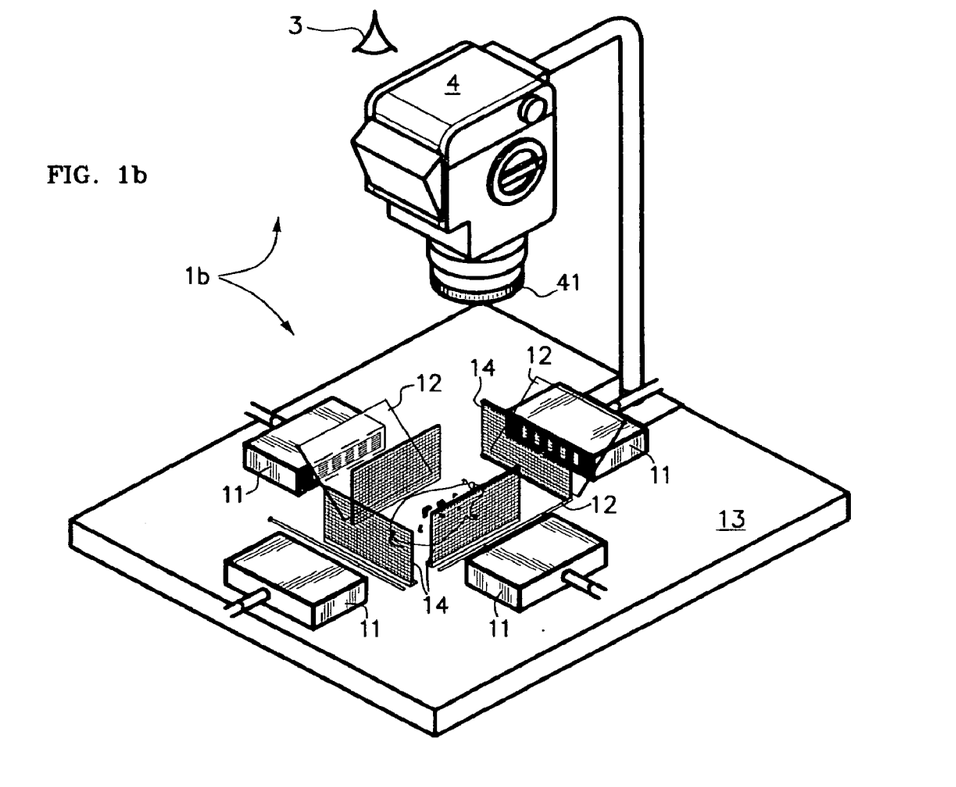
FIG. 1b is a diagrammatic view of a preferred illumination and viewing apparatus in accordance with the present invention.
Figure 2:
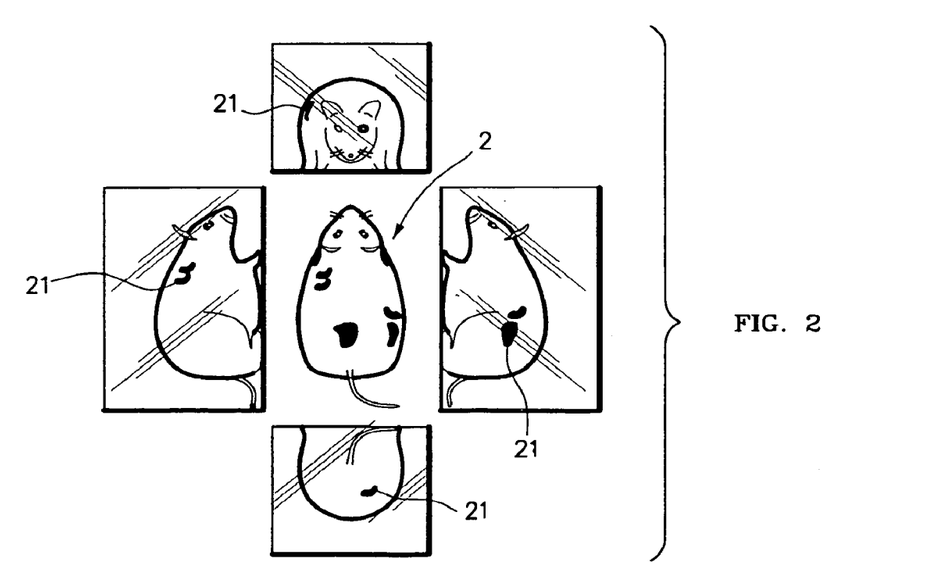
FIG. 2 is a diagram of an image of a specimen mouse realized with the preferred illumination and viewing apparatus in accordance with the present invention previously seen in FIG. 2

A diagrammatic view of a first, rudimentary, embodiment of an illumination and viewing apparatus 1a in accordance with the present invention is shown in FIG. 1a. A perspective view of a preferred embodiment of the same apparatus 1b—minus two electronic sensors and control loops for sake of clarity of illustration—is shown in FIG. 1b. A composite view obtained by the preferred apparatus of FIG. 1b is shown in FIG. 2.

Each illumination and viewing apparatus 1a, 1b consists of multiple illumination sources 11 illuminating a specimen 2 (not part of the present invention; shown in phantom line) through respective multiple dichroic mirrors 12. Thus multiple light beams illuminating specimen 2. The reflections of all such separate light beams as illuminate the specimen 2 from the specimen 2 are, as reflected in the dichroic mirrors 12, simultaneously visible along a viewing axis and to an observer's eyeball 3 or to a camera 4 (neither of which is part of the present invention).

The lens of camera 4 is covered with a bandpass filter 41, as is conventional. The filter 41 serves to substantially block the illuminating radiation from illumination sources 11—which radiation is otherwise always bright in the image seen by camera 4 (or eyeball 3)—and to substantially pass the fluorescent emissions induced by this illumination within specimen 2. For example, if the illuminating radiation was energetic blue light, and the induced fluorescence of both (1) green and (2) red colors, then the filter 41 would substantially block blue light, but pass both green and red light. An optical objective stage, or viewing tube (not shown) may optionally be included.

At least (1) the emitting ends of the multiple illumination sources 11, (2) a cradle (not shown) for the specimen 2 (not part of the present invention), (3) the dichroic mirrors 12, and (4) the optional optical objective stage, or viewing tube (not shown), are held in alignment upon a stage, and by an instrument frame, 13—as is common in the optical instrumentation arts.

The paths of light ultimately appearing in such composite image as appears to the observer's eyeball 3, or to the camera 4, is thus as follows. Light from each of the multiple illumination sources 11 passes in part through an associated one of the dichroic mirrors 12, whereupon a portion of these passed light beams is either (1) are reflected from corresponding regions of the specimen 2, or, more commonly, (2) being absorbed induces fluorescent light emissions from selected areas 21. Those portions of the incipient light that are reflected from each respectively illuminated region of the specimen, and/or the induced fluorescent emissions, are substantially reflected in the dichroic mirrors 12 and are directed to the observer's eyeball 3, or the camera 4.

A first photoelectric sensor 14, filtered or tuned so as to be sensitive to, most normally, an expected color (i.e., wavelength, or frequency) of fluorescent emission intercepts emitted fluorescent light over a sufficiently broad area of one optical path so as to detect the (cumulative, aggregate) fluorescent light emissions (if any be present). The sensor 14 operates through an electrical path 15 to control a variable power source 16 which in turn powers a variable light 17 that shines through a fiber optic bundle 18 (or a light pipe or the like) to energize a respective one light source 11. This control loop operates to a preset level to brighten the light 17, and the corresponding one light source 11, when the fluorescent emission is dim, and to make less bright the light 17, and the corresponding one light source 11, when the fluorescent emission is bright. Similar illumination light intensity control sensors and paths, not shown, appear on other ones of the illumination paths leading to the light sources 11.

The control of illumination intensities, and also colors (i.e., wavelengths, or colors, may optionally more preferably be in accordance with the related patent application for CONTROLLED-INTENSITY MULTIPLE-WAVELENGTH MULTIPLE-AXIS ILLUMINATION OF MACROSCOPIC SPECIMENS FROM A SINGLE LIGHT SOURCE FROM SPECIAL MASKS, FILTERS AND/OR BIFURCATED CABLES. In this configuration multi-color (dual color) is preferably realized along each of four illumination axis (specimen left, right, front and rear as is shown in FIG. 1b) by two only lamps each of which can have its light output adjusted. The light output is commonly so adjusted by changing the (d.c.) voltage to the lamp—like as is illustrated for one only illumination axis in FIG. 1a—with the light output of the lamp being proportionately changed. The light output of each lamp is then preferably projected through one or more associated color, or neutral density, filters are within optical paths leading into each of two ends of one or more bifurcated, or, still more preferably, an "X" cross, fiber optic cables. The light outputs of two lamps—which lamps are most commonly at different intensities and also different colors (i.e., wavelengths, or frequencies and the light in each path from each lamp which may be filtered—is thus distributed, normally equally, among some two "X"-cross fiber optic cables, and to, ultimately, four separate cable ends, illustrated as 11 in FIG. 1*b*, where illuminating light is produced. Use of these bifurcated, or "X"-cross fiber optic cables—as is more completely explained in the related patent application—can result in some diminishment in the flexibility with which the illuminating light may be independently adjusted in each illumination path, and between illumination paths, but the economies of illuminating light production and distribution within the apparatus are much improved.

It should also be understood in FIGS. 1*a* and 1*b* that (1) there may be, and commonly is, ambient, or laboratory, lighting, and/or (2) the specimen mouse 2 may also be illuminated from above (illumination source not shown) as required or desired.

Continuing in FIG. 1*a*, another optical sensor 19, tuned so as to be sensitive to, most normally, the presence of a specimen animal such as the mouse 2 within the viewing field, operates through an electrical path 111 to trigger an exposure by the camera 4. A one shot trigger circuit, which circuit is normally internal and innate to the trigger control circuit of the camera 4, ensures that one only exposure is taken per specimen animal. In other words the specimen stage where is shown positioned mouse 2 in FIGS. 1*a* and 1*b* must be at least momentarily vacated between successive exposures.

Successive mice 2 may be guided into position by a mouse-sized version of a "racetrack", or a "cattle chute" 5. One simple implementation uses clear plastic tubing of approximately the same diameter as is used to secure golf clubs within golf bags, substantially as shown. The mice are normally "herded" from their cage 53 into the tube 51, where they are forced to queue single file. One or more pairs of simple gating mechanisms, such as retractable rods 52, are selectively manually operated by the experimenter and observer so as to permit one 2 mouse at a time, seriatim, to enter the viewing station, become detected by the sensor 19, and trigger an exposure by the camera 4. If the tube 51 interferes with the viewing and observation of the mouse 2, then the "racetrack", or a "cattle chute" 5 can be relieved at this region, and the mouse 2 restrained by other means, such as a simple grid of spaced parallel wires in the outline of a tube, or box. Note that, insofar as the tube 51, or a wire restraining mechanism, or anything else constraining the specimen mouse 2 at the viewing station shows in the composite image rendered to the camera 4, or to the eyeball 3, then, insofar as the construction of this restraint is of known precision dimensions, the appearance of this restraint within the image can support dimensionally sizing both the specimen mouse 2 and any visible (fluorescent) tumors (or bodies or the like) also appearing within the image. This is but another example that the dimensional scale of element 14*a*—shown in and later discussed in conjunction with FIG. 3*a*—and be realized by diverse means.

In FIG. 1*b* the rudimentary apparatus of FIG. 1*a* is extended and expanded by the incorporation of (1) illumination sources 11 and accompanying dichroic mirrors 12 along yet another set of viewing axis, as well as new filter elements 14, seen in greater detail in FIG. 3. The multiple light sources 11 may in particular be based on bifurcated fiber optic cables, as is taught in the related patent application for CONTROLLED-INTENSITY MULTIPLE-WAVELENGTH MULTIPLE-AXIS ILLUMINATION OF MACROSCOPIC SPECIMENS FROM A SINGLE LIGHT SOURCE FROM SPECIAL MASKS, FILTERS AND/OR BIFURCATED CABLES.

Before further exposition of added filter elements 14, a diagram of an image of a specimen mouse realized with the preferred illumination and viewing apparatus 1*b* in accordance with the present invention may be noted in FIG. 2. The view is clearly "multi-axial", and is in fact along four axis mutually perpendicular by pairs. The view is also panoramic, being 360° around the specimen mouse 2 in one plane and some 180° over the "top" of the mouse in an orthogonal plane.

Figure 3A:
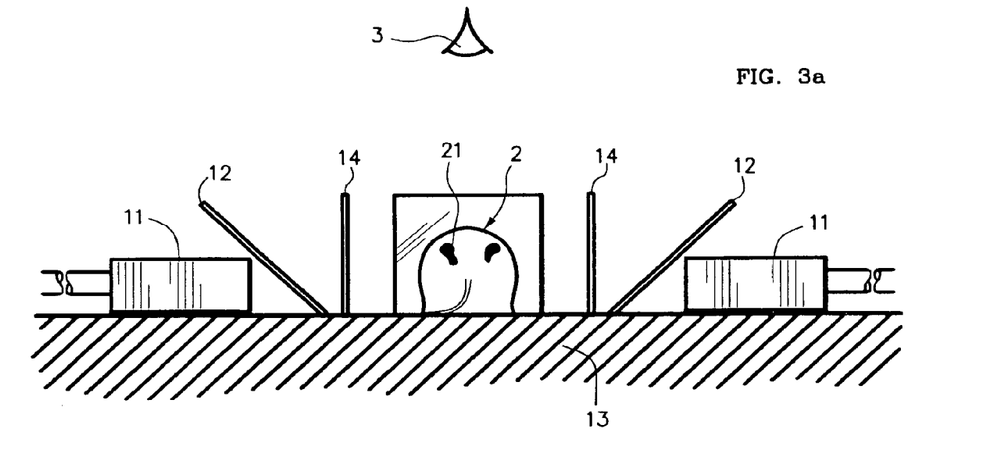
Figure 3B:
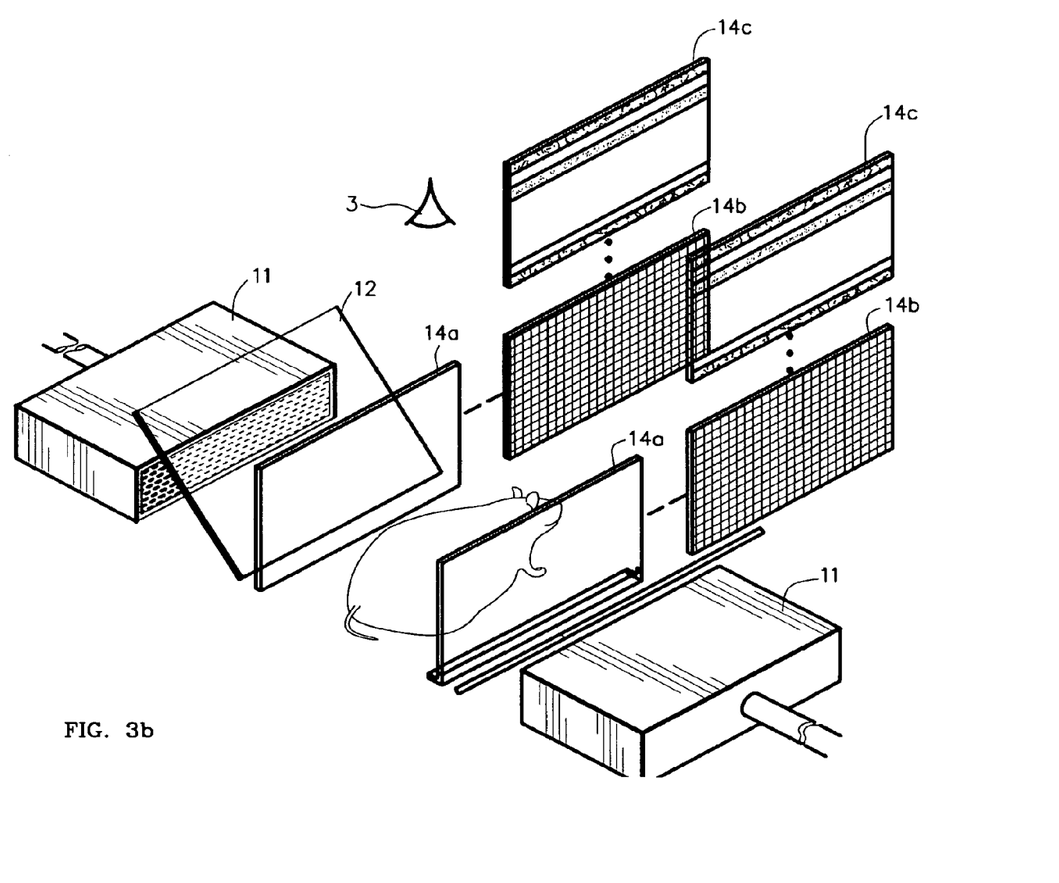

An expansion, and extension, accorded the preferred illumination and viewing apparatus 1*b* in accordance with the present invention by the addition of filter elements 14 is shown in greater detail in FIG. 3, consisting of FIGS. 3*a* and 3*b*. By comparison with FIG. 1*a*, the several added elements 14 may be noted in FIG. 1*b* and in FIG. 3. These elements 14 may be any of (1) scales or grid reticules 14*a*, (2) color filters 14*b*, and/or (3) fluorescent image calibration step wedges 14*c*, all as are best visible in FIG. 3*b*.

In the case of a scale and/or grid reticule element 14*a*, the element may be a clear glass plate or the like marked with a linear, and/or a reticular grid, scale. The grid reticule element 14*a* may alternatively be in the form of a framed screen or wire grid where parallel and/or intersecting wires or the like span a central aperture bounded by a generally rectangular frame. This scale then appears within the corresponding fields of the composite image, and provides a basis by which the image, and items such as specimen 2 and fluorescent fields 21 appearing therein, may be sized. Notably, this scale can also be impressed upon each or any of the dichroic mirrors 12, in which case no separate scale element 14*a* needs be included. Still furthermore, any grid scale can be derived from an enclosure 5 (shown only in FIG. 1*a*) of the specimen mouse 2, as was discussed above.

In the case of a scale and/or grid reticule element 14*a*, the element is preferably marked with a linear, and/or a reticular grid, scale. This scale then appears within the corresponding fields of the composite image, and provides a basis by which the image, and items such as specimen 2 appearing therein, may be sized. Notably, this scale can also be impressed upon each or any of the dichroic mirrors 12, in which case no separate scale element 14*a* needs be included.

The alternative, or additional, element 14*b* is in the general nature of a color filter. It may be any of a passband filter of color (i.e., wavelength, or frequency), or a neutral density intensity attenuation filter, or any other type and purpose for which filters are commonly used. A filter element 14*b* may commonly be inserted within the optical path, as illustrated, in order to adjust, or selectively adjust, the intensity and/or color and/or color temperature of the composite image (shown in FIG. 2), or—importantly—selected regions of this image. The composite image regions adjusted by each filter element 14*b* are, of course, only those regions in which the filter element 14*b* is within the optical path.

The element 14 may still further be a fluorescent image calibration step wedge 14*c*, as is taught within the related patent application for a FLUORESCENT IMAGE CALIBRATION STEP WEDGE, AND USE THEREOF IN ILLUMINATION FOR FLUORESCENT IMAGING. Such a fluorescent image calibration step wedge element 14*c* is essentially a scale by which any, and most preferably all, of the color properties of color fields appearing within the composite image may be measured. In the illustration of FIG. 3*b* a fluorescent image calibration step wedge element 14*c* having two color scales, such as might besuit by way of example a green fluorescence and a red fluorescence, is illustrated. By comparison of a portion of the image, such as a an image portion 21 of a tumor that is fluorescing green, with an appropriate (green scale) portion of the fluorescent image calibration step wedge element 14c, then the true color, intensity, etc., of this image portion may be rigorously determined.

In general the present invention has thus been seen to enable (1) multi-axial, or panoramic, imaging of a macroscopically-sized specimen, (2) automatic, and automatically calibrated, balanced imaging of such specimen, and particularly of multi-colored fields of fluorescent emission from regions of the specimen as such multi-colored fluorescent emissions are induced by illuminating light along each of multiple axis, and even (3) semi-automated positioning of successive specimens for observation and imaging, with photographing of each specimen being automatic.

In accordance with the preceding explanation, variations and adaptations of the apparatus and method for illuminating and panoramically viewing a macroscopically-sized specimen along a single axis at a single time in accordance with the present invention will suggest themselves to a practitioner of the optical arts.

For example, the dichroic mirrors 12 need not be made straight and in segments to surround specimen 2, but rather one single dichroic mirror 12 in shape of a shallow bowl could be made and used to support continuous panoramic illumination and viewing.

In accordance with these and other possible variations and adaptations of the present invention, the scope of the invention should be determined in accordance with the following claims, only, and not solely in accordance with that embodiment within which the invention has been taught.

What is claimed is:

1. An apparatus for illuminating a macroscopically-sized specimen for, upon at least one time, observation along a single viewing axis, the apparatus comprising: a stage for supporting a specimen to be observed; one or more first illumination sources radiatively illuminating the specimen upon the stage so that at least some radiation returned from the specimen will be returned along the viewing axis; at least one dichroic mirror positioned so that at least a portion of the specimen not directly observable along the viewing axis will be reflected in the mirror so as to become observable along the viewing axis; and one or more second illumination sources radiatively illuminating the specimen on the stage through the at least one dichroic mirror so that at least some radiation reflected from that region of the specimen not directly observable along the viewing axis will become reflected by the dichroic mirror and will become observable along the viewing axis.

2. The apparatus according to claim 1 wherein the at least one dichroic mirror comprises: a plurality of dichroic mirrors at least two of which plurality are oppositely positioned about the specimen upon the stage; wherein radiation directly reflected from the specimen along the viewing axis permits an observation called a top view while radiation from the specimen reflected by the at least two dichroic mirrors permits observations called left and right side views.

3. The apparatus according to claim 1 wherein at least one of the one or more first illumination sources is directly illuminating the specimen upon the stage.

4. The apparatus according to claim 3 wherein two first illumination sources directly illuminate the specimen upon the stage.

5. The apparatus according to claim 1 wherein at least one of the first and the second illumination sources is a fiber optic illumination source.

6. The apparatus according to claim 1 wherein radiation emitted from at least one of the first and the second illumination sources is suitable so as to induce fluorescent emission in the specimen.

7. The apparatus according to claim 1 that, further comprises: a selectively regionally transparent and opaque grid or rule mask, located between the at least one dichroic mirror and the specimen upon the stage, for selectively blocking both radiation from the at least one second illumination source through the at least one dichroic mirror to the specimen, and also such radiation reflected from the specimen as is further reflected by the at least one dichroic mirror along the viewing axis, so that a grid pattern or rule scale visually appears upon an image of those specimen regions that are illuminated through, and that are viewed through, the mask.

8. The apparatus according to claim 1 that, between the at least one dichroic mirror and the specimen upon the stage, further comprises: a color filter.

9. The apparatus according to claim 1 that, between the at least one dichroic mirror and the specimen upon the stage, further comprises: a fluorescent image calibration step wedge.

10. An improvement of an apparatus holding and illuminating a macroscopically-size three dimensional specimen so that about one-half of the specimen's surface may be viewed at one time along a single viewing axis, improvement comprising: a dichroic mirror positioned so that at least a portion of the specimen that is not directly observable along the viewing axis will be reflected in the mirror so as to become observable along the viewing axis; and an illumination source illuminating the specimen on the stage through the at least one dichroic mirror; wherein at least some illumination arising from the illumination source that is reflected from that region of the specimen not directly observable along the viewing axis will become reflected by the dichroic mirror and will become observable along the viewing axis; wherein more than one-half of the surface of specimen is panoramically viewable along the single viewing axis at the one time.

11. The improvement to a specimen holding and illuminating apparatus according to claim 10 wherein two dichroic mirrors are oppositely positioned about the specimen upon the stage so that each does permit observation of at least some regions of the specimen's surface not directly observable along the viewing axis; and wherein the illumination source serves to illuminate the specimen through each of the two dichroic mirrors; wherein illumination directly reflected from the specimen along the viewing axis permits an observation called a top view while radiation from the specimen reflected by each of the two dichroic mirrors simultaneously permits observations called left and right side views.

12. The improvement to a specimen holding and illuminating apparatus according to claim 10 wherein the illumination source serves to illuminate the specimen through the dichroic mirror with radiation suitable to induce fluorescent emission in the specimen.

13. The improvement to a specimen holding and illuminating according to claim 10 further comprising: a selectively regionally transparent and opaque grid or rule mask, located between the dichroic mirror and the specimen upon the stage, for selectively blocking both illumination from the illumination source passing through the dichroic mirror to the specimen, and also illumination reflected from the specimen as is further reflected by the dichroic mirror along the viewing axis, so that a grid pattern or rule scale visually appears upon an image of those regions of the specimen's surface that are illuminated through, and that are viewed through, the mask.

14. The improvement to a specimen holding and illuminating according to claim 10 further comprising: a color filter located between the dichroic mirror and the specimen upon the stage.

15. The improvement to a specimen holding and illuminating according to claim 10 further comprising: a fluorescent image calibration step wedge located between the dichroic mirror and the specimen upon the stage.

16. A method of illuminating a macroscopically-sized specimen for, upon at least one time, observation along a single viewing axis, the method comprising: supporting a specimen to be observed upon a stage; first radiatively illuminating the specimen upon the stage so that at least some radiation directly reflected from the specimen will be returned along the viewing axis; positioning a dichroic mirror so that at least a portion of the specimen not directly observable along the viewing axis will be reflected in the mirror so as to become observable along the viewing axis; and second radiatively illuminating the specimen on the stage through the dichroic mirror so that at least some radiation reflected from that region of the specimen not directly observable along the viewing axis will become reflected by the dichroic mirror and will become observable along the viewing axis.

17. The method according to claim 16 wherein positioning comprises positioning two dichroic mirror to be on opposite side of the specimen upon the stage; and wherein radiation directly reflected from the specimen along the viewing axis permits an observation called a top view while radiation from the specimen reflected by each of the two dichroic mirrors permits observations called left and right side views.

18. The method according to claim 16 wherein the first radiatively illuminating serves to directly illuminate the specimen upon the stage.

19. The method according to claim 16 wherein the first radiatively illuminating is with light from a fiber optic illumination source adequate to excite fluorescence.

20. The method according to claim 16 wherein the first radiatively illuminating, or the second radiatively illuminating, or both the first and the second radiatively illuminating is with radiation suitable so as to induce fluorescent emission in the specimen.

21. The method according to claim 16 further comprising: interposing a selectively regionally transparent and opaque grid or rule mask between the dichroic mirror and the specimen upon the stage so as to selectively block radiation from the second radiatively illuminating en route from the dichroic mirror to the specimen, and also some of this same radiation that, as reflected from the specimen, is en route from the specimen to the dichroic mirror, so that a grid pattern or rule scale will visually appear upon an image of those specimen regions that are illuminated through, and that are viewed through, the mask.

22. The method according to claim 16 further comprising: interposing a color filter between the dichroic mirror and the specimen upon the stage.

23. The method according to claim 16 further comprising: interposing a fluorescent image calibration step wedge between the dichroic mirror and the specimen upon the stage.

* * * * *